(12) United States Patent
Yeh et al.

(10) Patent No.: US 7,588,935 B2
(45) Date of Patent: Sep. 15, 2009

(54) VIRAL VECTOR FOR INDUCING GENE INACTIVATION OF PLANTS AND APPLICATION THEREOF

(75) Inventors: Hsin-Hung Yeh, Taipei (TW); Hong-Hwa Chen, Taipei (TW); Shiang-Jia Lu, Taipei (TW)

(73) Assignee: National Taiwan University, Taipei (TW)

( * ) Notice: Subject to any disclaimer, the term of this patent is extended or adjusted under 35 U.S.C. 154(b) by 322 days.

(21) Appl. No.: 11/376,269

(22) Filed: Mar. 15, 2006

(65) Prior Publication Data

US 2007/0220633 A1 Sep. 20, 2007

(51) Int. Cl.
*C12N 15/82* (2006.01)
*C12N 5/14* (2006.01)

(52) U.S. Cl. .................... 435/320.1; 800/278
(58) Field of Classification Search ......... None
See application file for complete search history.

(56) References Cited

OTHER PUBLICATIONS

Wong et al. 1997, Arch Virol 142:383-391.*

* cited by examiner

*Primary Examiner*—Anne Marie Grunberg
*Assistant Examiner*—Li Zheng
(74) *Attorney, Agent, or Firm*—Morris, Manning & Martin LLP; Tim Tingkang Xia

(57) ABSTRACT

The invention relates to a method to inactivate plant genes. In one embodiment, the method comprises the steps of providing a viral vector comprising a cDNA sequence reverse transcribed from RNA of Cymbidium mosaic virus; constructing a recombinant plasmid containing a homologous gene fragment of the plant and the viral vector; preparing transcripts of the plasmid through in vitro transcription; infecting the plant with the transcripts; and forming siRNA from the transcripts to inactivate the homologous gene.

5 Claims, 9 Drawing Sheets
(9 of 9 Drawing Sheet(s) Filed in Color)

A

M  M1  CymMV-pro60-GFP  CymMV-pro100-GFP

Genome rRNA

B

M  TMV-GFP  M1  CymMV-pro60-GFP  CymMV-pro100-GFP

Genome rRNA

FIG. 5

SEQUENCE LISTING

<160> NUMBER OF SEQ ID NOS: 28

<210> SEQ ID NO 1
<211> LENGTH: 6226
<212> TYPE: DNA
<213> ORGANISM: Cymbidium mosaic virus

<400> SEQUENCE: 1

| | | | | | |
|---|---|---|---|---|---|
| ggaaaaccaa | aacctcacgtc | taatccgcta | tccgagcgaa | atagcagccc | cagcataggc | 60 |
| aatatcgcgc | tccatggccc | gagtacgtga | caccccttgac | aggctccgtg | atccgtcggt | 120 |
| ccttacctca | attaacgagg | aagcccaccg | acatatccgc | cctgtccttg | cctcggcact | 180 |
| cgtaaactgc | ccttacgcgt | tgaccgagga | agaggccgac | tgtctcgaaa | atctcggcgt | 240 |
| gacagtcaat | cccttcgcca | tccaaacgca | tacacatgct | gcagcaaaaa | ctgttgaaaa | 300 |
| tcgcatgttg | gaaattgttg | gcaccccacct | tcctaaagaa | ccctccacct | tcatattcct | 360 |
| taagcggagc | aagcttcgct | acctacgacg | cgccgccaac | aacaaagaca | tatttcaaaa | 420 |
| ccaacacatt | gagcctaaag | acttattgcg | ttacgatgac | gagtcttgtg | aagcaatgcc | 480 |
| agaatgctcc | acaagcacag | cctacatcag | cgatgctctc | catttcttga | gctacgctca | 540 |
| gcttgggaaa | atattccagg | attctcccaa | gctaaaaatt | ctgctggcaa | ccctggtcct | 600 |
| ccccgtggaa | gccctccata | ggcacccatc | tctttaccct | gccatctaca | ctttgaacta | 660 |
| ccataaagat | ggctttgaat | atatacccgg | caatcacgcc | ggaggtgctt | acttccacga | 720 |
| gtactccact | ctgcagtggt | tgactctcgg | aaaactaatt | atcaacgatc | ctttgaaagt | 780 |
| aaagaaaccc | cttactctta | ctgtacagct | aatagaaagt | ctaggggcta | accatctttt | 840 |
| acttatcacc | cgaggggatc | ttcgcacacc | caaactgcgg | acattcgcta | aagatcccca | 900 |
| tgttctacta | ccacaaatat | tccatcctaa | gggtatgaat | gcgaacaaac | cattgtccaa | 960 |
| acgtagagct | atgcagttgt | ggctctacgc | caaatctgtt | aaagaggtga | gcgaacggga | 1020 |
| tctttatgct | aaggtgaggc | aattgatccc | gacttctgag | ttagaccttt | ttgaccctgt | 1080 |
| ggaggtgacc | catttggtca | attacttact | attcatcagt | cacctttcct | ccgtatcttc | 1140 |
| gtatgacgac | atcttgtcgt | ctaatatctt | ccaacatttc | accattccaa | tcaagaacaa | 1200 |
| gatacgggaa | ttggtccagc | tattcaccgg | agcggaccaa | tttaatcaac | tgctcaaagc | 1260 |
| tctcgactgg | caaacatttt | cgtactctat | gccagtagag | accatccata | cacgtgcggc | 1320 |
| caattatcaa | gtcgctaaaa | cgcttcgcat | gtgcagagac | ctaccatgcg | atgaatatga | 1380 |
| tcgtgtaaag | gatgtcctca | aacagctccc | tgacggagtg | acgttgtttg | aggaaaacga | 1440 |
| taagcaagat | ccctcaagct | ctgaaaccga | ggactctgag | gatgacactg | actccgtcga | 1500 |
| cttcaacctt | ccccccactc | atgacttgcc | cccaaacttt | gatcctctag | acaagggcaa | 1560 |
| gtccattatc | gttgacaccg | acaacccctc | aacttccacg | gcacctgccg | tcacttttgc | 1620 |
| tgccggtatc | aactcctcag | cctccacaaa | tatttcattt | ggaagcttca | cacctgaggc | 1680 |
| tgaggccacc | ccccctcctc | ccatggaaaa | gttaccatgg | gatctttgga | ttcccctact | 1740 |
| ggaacaacat | ggctttaaag | gaaagagtaa | gctgtacaag | cccacgggtg | aactaatctg | 1800 |
| ccccataact | gaaatcaaaa | cagttcccca | ctgcccccttt | cccgataaag | tcccggatgg | 1860 |
| ttgtgtgctt | gcgctcaaat | ctattaagcg | tttcgccaca | aaaatgacta | tgctcagttc | 1920 |
| tcgagcctcc | gcctacactt | ctgacattaa | gaatagtagg | actggaaagc | tcctacccgc | 1980 |
| catgaacatg | ccctggaaag | cctctctcgc | ctatgtcact | caacatggtg | atagagaaat | 2040 |

-continued

```
tcctggcgtc gtgatccatg gcgccggtgg ctgtggcaaa tcttatgcca tccaaaaatg    2100
gttgagaagc tgctctgatc cttgcgcagc tactgtggta tgcccaactc tagaactacg    2160
taatgactgg ctcaataaga tcggaagcta cgaacaaacg aatatcaaaa ctttcgagaa    2220
agctttaatt cagccagtca acaacgtagt tatctttgat gattacacca agctaccccc    2280
tgggtacatc gagaccatgg tgtaccatca ccacaacctc gacctgatca tattaactgg    2340
ggatcctatg cagagtgcct accatgaaac taacagagat gcctacatct ctttaatacc    2400
tgatgcctct gccatcttta gtgagtactg tgagttcaac atcaacgcca cccaccgtaa    2460
tgtagccgaa ctcgcttgcc tcctcggcgt ctattctgaa cgccaaggca aactcactgt    2520
ttccttcagc gcagcccac tttctaaagg taaagtaccc attctggtac cctctagaat     2580
gaagcaagag gcttttgctg atgtcggcaa ccgttgcatg acttatgccg gttgccaggg    2640
tctcactgcc cctaaaatcc aaattttgat agacaaccac actacgttct gctccgaaca    2700
aacattatac acttgtctat cacgagctgt ggaccaaatc cacttcatta acactggtcc    2760
caactcacag gctttctgga ccaaattaga atccacgccg tacctaaaag ctttcctcga    2820
taattaccgt gaggaacaaa ctgaacggct aacatctacc gccccagagc ctgaagtccg    2880
tgagccagca gccccaaaaa cgcatatccc tgtcgaaaat acatctggct tacgtatttc    2940
tgcacttgac ctgccggaaa agcactctcg cgagattttc aacaaggcgc atggcttttc    3000
caatgctatt cagggagatg gcgttgctcc catgttccag catcaacagg caaaggacga    3060
aacccttttc aaggctacca tagatgctag actctctata acacatccta atgaaaacaa    3120
aagagagttt gccatgaaga aagatactgg ggacgtcctt tttatcaatt acaaagctat    3180
aatgaatcta cctcatgagc ctgttccttt cgaacctcgt ctctggaaca tctgcaaagc    3240
tgaagtgcag aacacatacc tagccaaacc cattgcaaat ctcatcaatg gtaccttaag    3300
gcaatcaccc gattttccag ccaataaaat agccttattc ctgaaatcgc aatgggtaaa    3360
gaaaattgag aaaattggag ccataccagt taaacctgga cagactattg catcatttat    3420
gcaagagact gttatgctgt atggcaccat ggcacgctac ctccgtaaga tgcggcaaag    3480
atttcaaccc gcacatatat ttatcaattg tgaaaagact ccggaggact caacaaatt    3540 cgtacttgaa cactggtcca acaagcaggt tgcccatact aacgatttta ctgcttttga    3600
ccagtcacaa gatgctgcca tgctccaatt tgaagttatc aaagctaggt acttcaatat    3660 cccccgaggat gttatagaag gatacatcca aattaagctc actgctgaaa tcttcctcgg    3720
gacactttcc atcatgcgcc tatctggtga agggccaacc ttcgacgcca atactgaatg    3780
ctctattgcc tacaacgcca ccagataccc tattaatgaa gacgtcacac aagtatacgc    3840
cggtgacgac atggctatgg accatgtgtg ccctgagaag aagagcttca agctttgga    3900 aaagaaacta aaattgacct caaaacctct ctatccaaag caaaaacctg agactgggc    3960 cgatttctgc ggctggacta taacgcctta tggcatcatc aagaatccta agaaacttga    4020
tgcatgccta caattgcaca cccaactggg cgatgccgat aaagtcgcta ggtcatatgc    4080
actcgacgcc aaatatgctt atgatctggg cgatcgcatt catgaggttc tgaatgttga    4140
tgaaatgacc agccacttca atgttataag acagttgcac aaactgcatc aacaagatgt    4200
actggtccca cctgagacta ccgtagccac agcggtaaag tctcaacctg acgtggagga    4260
tctgtggctc cgtgcgctta gcttccctga ctggacggac cgcgcccaac ttttaaaacg    4320
gggttaattt tgatggagct agcgtactta gttagattac tagagcacaa taaattcgag    4380
```

-continued

```
cgcaccaatc tgccccttc ctcaccctta gttgtacacg gaattgctgg cagtggaaaa    4440
tccaccatcc tcacaacttt ctatcaccat tacccggctc accccatctt ctcacacagt    4500
cccacattgc ttgaccctag caaccgcata taccaacagt gcatcactac tgattctgtg    4560
ccagacggtg ctatcgtaga cgagtacaat tacaaagcgc tcgactactc tcactgtcta    4620
gccctcttcg gtgatccact ccaacttcca cattcacttc aaccccacta ctactctagt    4680
cgcacccacc gctacggtcc caagctcacc agcctactca cgacctctt ccacctttct    4740 atcacttctc ttgcccccgt tgacagcctt gattacgctg atccttttgc tgtcgacccc    4800
tctggattta ccattgctga cgaggaagtg taccacttcg tctctcagca ggttcctggc    4860
actttgttgc cgctcgatac tgtaggctta gaatattcta gtgttagctt ttattgcagt    4920
gatctccgac gctgtgtcgt actaaggcca ctcagcacct tcatcgctct cacccgcgcc    4980
aagggcaacc tcattatctt cgatttcaat gccaggtcta gttccaccac ctgaccactc    5040
caaatcactc ttcgtccttg ctattggtat aactgtggtc tccgcattat ttgtgctaaa    5100
gtcccacact tttccgattg caggcgacaa tattcaccgc ttcccctccg gcggccaata    5160
taaagacggt actaagcaga taaactactg tccgcctact catgctaggt acccgaaata    5220
tcctgactac aagtggcttg ccgctaccgc cgccatcgtc atccctctct gcctatatat    5280
ttcctaccat cctggcaata atattcgccg tatttgccct tgttgcaata catatccacca    5340 cccctgagcc cttctgtacc atacacatag acggggcgtc tattactatc actaactgcc    5400
ccgatcctgc agctatatta aataaagtag ccataggccc ctggcgaggg ttaagttacc    5460
acaataattt gaaataatca tgggagagcc cactccaact ccagctgcca cttactccgc    5520
tgccgacccc acttctgcac ccaagttagc cgacctggct gccattaagt actcacctgt    5580
tacctcctcc atcgccacac ccgaagaaat caaggccata acccaattgt gggttaacaa    5640
ccttggcctc cccgccgaca cagtaggtac cgcggccatt gacctggccc gcgcctacgc    5700
tgacgtcggg gcgtccaaga gtgctaccct gctcggtttc tgccctacga acctgatgt    5760 ccgtcgcgcc gctcttgccg cgcagatctt cgtggccaac gtcaccccccc gccagttttg    5820 cgcttactac gcaaaagtgg tgtggaattt gatgctggcc actaacgatc cgcccgccaa    5880
ctgggccaag gctggtttcc aggaggatac ccggtttgcc gcctttgact ttttcgatgc    5940
cgtcgattcc actgccgcgc tggagcctgc tgaatggcag cgccgcccta ctgaccgtga    6000
acgtgctgcg cactcaatcg ggaagtacgg cgcccttgcc cgtcagcgta tccaaaacgg    6060
caacctcatc accaacattg ccgaggtcac caagggccat tttggctcca ccaacactct    6120
ttatgctctg cctgcacccc ctactgaata acgccaaact taataaggcg tgtggttttt    6180
taaagtttgt ttccactact ggcataataa gtttagccag ataaat              6226
```

<210> SEQ ID NO 2
<211> LENGTH: 121
<212> TYPE: DNA
<213> ORGANISM: Cymbidium mosaic virus

<400> SEQUENCE: 2

```
ctattactat cactaactgc cccgatcctg cagctatatt aaataaagta gccataggcc    60
cctggcgagg gttaagttac cacaataatt tgaaataatc atgggagagc ccactccaac   120
t                                                                   121
```

<210> SEQ ID NO 3
<211> LENGTH: 81

-continued

<212> TYPE: DNA
<213> ORGANISM: Cymbidium mosaic virus

<400> SEQUENCE: 3
aaataaagta gccataggcc cctggcgagg gttaagttac cacaataatt tgaaataatc 60
atgggagagc ccactccaac t 81

<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4
gaaataatca tgggagagcc 20

<210> SEQ ID NO 5
<211> LENGTH: 21
<212> TYPE: DNA
<213> ORGANISM: Artificial
<220> FEATURE:
<223> OTHER INFORMATION: primer

<400> SEQUENCE: 5
agtttggcgt tattcagtag g 21

<210> SEQ ID NO 6
<211> LENGTH: 25
<212> TYPE: DNA
<213> ORGANISM: Artificial
<220> FEATURE:
<223> OTHER INFORMATION: primer

<400> SEQUENCE: 6
aagctcttct tctcagggca cacat 25

<210> SEQ ID NO 7
<211> LENGTH: 53
<212> TYPE: DNA
<213> ORGANISM: Artificial
<220> FEATURE:
<223> OTHER INFORMATION: primer

<400> SEQUENCE: 7
cgcactagtt tttttttttt tttttttttt tttatttatc tggctaaact tat 53

<210> SEQ ID NO 8
<211> LENGTH: 54
<212> TYPE: DNA
<213> ORGANISM: Artificial
<220> FEATURE:
<223> OTHER INFORMATION: primer

<400> SEQUENCE: 8
gccaattaac cctcactaaa gaaaaccaaa cctcacgtct aatccgctat ccga 54

<210> SEQ ID NO 9
<211> LENGTH: 26
<212> TYPE: DNA
<213> ORGANISM: Artificial
<220> FEATURE:
<223> OTHER INFORMATION: primer

<400> SEQUENCE: 9

-continued

```
attgcctaca acgccaccag atacca                                           26

<210> SEQ ID NO 10
<211> LENGTH: 34
<212> TYPE: DNA
<213> ORGANISM: Artificial
<220> FEATURE:
<223> OTHER INFORMATION: primer

<400> SEQUENCE: 10
cactccaact cccgggagct gtcacttact ccgc                                  34

<210> SEQ ID NO 11
<211> LENGTH: 36
<212> TYPE: DNA
<213> ORGANISM: Artificial
<220> FEATURE:
<223> OTHER INFORMATION: primer

<400> SEQUENCE: 11
agtaagtgac agctcccggg agttggagtg ggctct                                36

<210> SEQ ID NO 12
<211> LENGTH: 20
<212> TYPE: DNA
<213> ORGANISM: Artificial
<220> FEATURE:
<223> OTHER INFORMATION: primer

<400> SEQUENCE: 12
aaataaagta gccataggcc                                                  20

<210> SEQ ID NO 13
<211> LENGTH: 21
<212> TYPE: DNA
<213> ORGANISM: Artificial
<220> FEATURE:
<223> OTHER INFORMATION: primer

<400> SEQUENCE: 13
ccccgatcct gcagctatat t                                                21

<210> SEQ ID NO 14
<211> LENGTH: 20
<212> TYPE: DNA
<213> ORGANISM: Artificial
<220> FEATURE:
<223> OTHER INFORMATION: primer

<400> SEQUENCE: 14
ggatccaagg agatataaca                                                  20

<210> SEQ ID NO 15
<211> LENGTH: 19
<212> TYPE: DNA
<213> ORGANISM: Artificial
<220> FEATURE:
<223> OTHER INFORMATION: primer

<400> SEQUENCE: 15
gagctcttaa agctcatca                                                   19

<210> SEQ ID NO 16
<211> LENGTH: 21
<212> TYPE: DNA
<213> ORGANISM: Artificial
```

```
<220> FEATURE:
<223> OTHER INFORMATION: primer

<400> SEQUENCE: 16
agggagtatg agagaactcg a                                              21

<210> SEQ ID NO 17
<211> LENGTH: 28
<212> TYPE: DNA
<213> ORGANISM: Artificial
<220> FEATURE:
<223> OTHER INFORMATION: primer

<400> SEQUENCE: 17
cggaattctt aaaaaccagg aaagcagt                                       28

<210> SEQ ID NO 18
<211> LENGTH: 919
<212> TYPE: DNA
<213> ORGANISM: Phalaenopsis sp.

<400> SEQUENCE: 18
gctgtgcttc tttttggggt tttcgcttct gctcctgaaa tctcttgcag tctcttttct    60
ttttcatcct gctctttccg ttttttgggt ggagatgggt cggggaaaga tagagatcaa   120
gagaatcgag aactcaacca accggcaagt gaccttctcg aagaggcgga atggaatcat   180
gaagaaggcg aaggagatca gcgtgctctg cgacgcccag gtttcgcttg tcatcttttc   240
cagccttgga aagatgtttg agtattgtag cccatccacc acgctgtcga agatgctgga   300
gaaataccag cagaactcgg ggaagaagct ctgggacgcc aagcacgaga acttgagcgc   360
ggagattgat cgtatcaaga aggaaaatga taatatgcag atcgaactca ggcatttgaa   420 agggaggat ctgaactctc ttaacccaaa agagcttatt ccgattgagg aagccctgca    480
gaatggtctc accagcgttc gggataaaca aatggactac ttgaagatgc taaaaagaa    540 tgaaaggatg cttgaagatg aaaataaaag gctcacatac ctattgcacc aacaacaaat   600
ggcaatggaa gggagtatga gagaactcga catcggctat catcataaag atcgcgagta   660
tgcggctcag atgccaatga cttttcgtgt ccaacccatt cagcccaact gcagggaaa    720 taagtaactg tgttagccta ctgctttcct gttgtttaaa tgaattatta tattaacttt   780
tggcagttct gtgagaatat gaaaacttat attgctaatt atcagatatg tgcttactag   840
tgatattcat attgtaactc tccaaactca ttagtaacta tggttaaata tttttatgtt   900
ctagtctatt ttgatatct                                                919

<210> SEQ ID NO 19
<211> LENGTH: 150
<212> TYPE: DNA
<213> ORGANISM: Phalaenopsis sp.

<400> SEQUENCE: 19
agggagtatg agagaactcg acatcggcta tcatcataaa gatcgcgagt atgcggctca    60
gatgccaatg acttttcgtg tccaacccat tcagcccaac ttgcagggaa ataagtaact   120
gtgttagcct actgctttcc tgttgtttaa                                    150

<210> SEQ ID NO 20
<211> LENGTH: 500
<212> TYPE: DNA
<213> ORGANISM: Phalaenopsis sp.
```

-continued

<400> SEQUENCE: 20

```
atgggtcggg gaaagataga gatcaagaga atcgagaact caaccaaccg gcaagtgacc      60
ttctcgaaga ggcggaatgg aatcatgaag aaggcgaagg agatcagcgt gctctgcgac     120
gcccaggttt cgcttgtcat cttttccagc cttggaaaga tgtttgagta ttgtagccca     180
tccaccacgc tgtcgaagat gctggagaaa taccagcaga actcggggaa gaagctctgg     240
gacgccaagc acgagaactt gagcgcggag attgatcgta tcaagaagga aaatgataat     300
atgcagatcg aactcaggca tttgaaaggg gaggatctga actctcttaa cccaaaagag     360
cttattccga ttgaggaagc cctgcagaat ggtctcacca gcgttcggga taaacaaatg     420
gactacttga agatgctaaa aaagaatgaa aggatgcttg aagatgaaaa taaaaggctc     480
acatacctat tgcaccaaca                                                 500
```

<210> SEQ ID NO 21
<211> LENGTH: 19
<212> TYPE: DNA
<213> ORGANISM: Artificial
<220> FEATURE:
<223> OTHER INFORMATION: primer

<400> SEQUENCE: 21

```
gaggggaaa gatagagat                                                    19
```

<210> SEQ ID NO 22
<211> LENGTH: 18
<212> TYPE: DNA
<213> ORGANISM: Artificial
<220> FEATURE:
<223> OTHER INFORMATION: primer

<400> SEQUENCE: 22

```
attgggctga atgggttg                                                    18
```

<210> SEQ ID NO 23
<211> LENGTH: 20
<212> TYPE: DNA
<213> ORGANISM: Artificial
<220> FEATURE:
<223> OTHER INFORMATION: primer

<400> SEQUENCE: 23

```
ggctcaatac tattgcacca                                                  20
```

<210> SEQ ID NO 24
<211> LENGTH: 21
<212> TYPE: DNA
<213> ORGANISM: Artificial
<220> FEATURE:
<223> OTHER INFORMATION: primer

<400> SEQUENCE: 24

```
ggacacgaaa agtcattggc a                                                21
```

<210> SEQ ID NO 25
<211> LENGTH: 20
<212> TYPE: DNA
<213> ORGANISM: Artificial
<220> FEATURE:
<223> OTHER INFORMATION: primer

<400> SEQUENCE: 25

```
ggctcaatac tattgcacca                                                  20
```

```
<210> SEQ ID NO 26
<211> LENGTH: 21
<212> TYPE: DNA
<213> ORGANISM: Artificial
<220> FEATURE:
<223> OTHER INFORMATION: primer

<400> SEQUENCE: 26
ggacacgaaa agtcattggc a                                              21

<210> SEQ ID NO 27
<211> LENGTH: 19
<212> TYPE: DNA
<213> ORGANISM: Artificial
<220> FEATURE:
<223> OTHER INFORMATION: primer

<400> SEQUENCE: 27
ccggatcagc aaaggttga                                                 19

<210> SEQ ID NO 28
<211> LENGTH: 19
<212> TYPE: DNA
<213> ORGANISM: Artificial
<220> FEATURE:
<223> OTHER INFORMATION: primer

<400> SEQUENCE: 28
aagatttgca tccctcccc                                                 19
```

VIRAL VECTOR FOR INDUCING GENE INACTIVATION OF PLANTS AND APPLICATION THEREOF

BACKGROUND OF THE INVENTION

1. Field of the Invention

The present invention relates to a viral vector, especially relates to a viral vector whose transcripts induce gene inactivation in plants.

2. The Prior Arts

Orchidaceous is one of the important plants with economic values. As for drugs derived from some orchids, more of them become important ornamental plants because of their enchanting flowers or showy leaves. Extensive breeding have also been conducted in *Phalaenopsis* spp. and more than 18,000 hybrids have been bred. Diversified flowers appearance may provide resources for elucidating evolution of genes involved in floral morphogenesis and their related function.

Methods to understand and analyze plant gene function are employed by using loss-of-function or gain-of-function techniques at present. Gene function analyzed by gain-of-function is generally accomplished through gene transformation, while loss-of-function is conducted through mutagen, transposon tagging, T-DNA insertion or homologous recombination. However, the abovementioned approaches are complicated, time-consuming and difficult to scale up the gene analysis. And methods for gene transformation are not established in many orchid species, such as *Phalaenopsis* spp., because of their lengthy life cycle. Two years are needed for flowering either with seed propagation or tissue culture after sowing. Therefore it is very time-consuming and unrealistic to analyze genes involved in floral development. In addition, genome sizes among various *Phalaenopsis* spp. are quite large, ranging from $1\times10^9$ to $6\times10^9$ bp/1C, and the multiploidy of commercial cultivars makes the genetic analysis more complicated.

Alternatively, gene silencing is used to analyze gene function recently. Virus induced gene silencing (VIGS) is an efficient and reliable method though there are many techniques being conducted to induce gene silencing. Gene transformation is not required in the VIGS process, which provides a quick and feasible way for plants with lengthy life cycle and transformation difficulties. The exact mechanism of VIGS remains unknown, so far it's been postulated that VIGS is related to host defense mechanisms to defend against foreign viral RNAs or transposon(s). Small interfering RNA (siRNA) has been observed in plants when foreign viruses invade plants. These siRNAs become, hybridize foreign viral RNAs and trigger nuclease to degrade viral RNA. Virus-induced gene silencing (VIGS) is a type of RNA silencing that is initiated by virus vectors carrying host genes being analyzed. The plants are infected with the transcripts to activate the RNA silencing of endogenous gene of host plants.

VIGS does not require the whole gene. It was reported that 23 nucleotides was enough to induce gene silencing (Plant J. 25, 417-25, 2001). This will alleviate problems of acquiring the whole cDNA. Compared with transformation of plants with sense and/or antisense gene approaches, the advantage of virus induced gene silencing (VIGS) is the relative speed. Moreover it suppresses the target gene RNA level after the seedling established, which will prevent suppression of some essential genes needed in development stages.

Kumagai et al. inserted partial phytoene desaturase (PDS) gene fragment into tobacco mosaic virus (TMV) cDNA clone (Proc. Natl. Acad. Sci. U.S.A. 92, 1679-83, 1995). In vitro transcripts derived from the infectious clone were used to inoculate plants. Initially infected plants show typical symptoms of TMV infection. One or two weeks later endogenous PDS mRNA could not be detected, and plants produced white leaves caused by decreasing of PDS gene expression. Ruiz et al. reported similar results using a potato virus X (PVX) based vector (Plant Cell, 10, 937-46, 1998). Burton et al. utilized a PVX vector to silence plant cellulose gene (Plant Cell, 12, 697-705, 2000). Most of the VIGS vectors constructed are applied in dicots. Among monocots, only Barley strip mosaic virus derived vectors have been developed by Holzberg et al. for VIGS (Plant J., 30, 315-27, 2002).

Orchid plants are monocots of economically importance, which own a large market. So far there is no report regarding the application of VIGS vectors in orchids. The gene function of orchid plants can be studied if a VIGS vector is developed to be applied in orchid plants. VIGS vectors help to screen genes of commercial values rapidly, especially towards flower morphology genes, as well as genes involved in related traits, which will have high commercial values.

SUMMARY OF THE INVENTION

From upon the abovementioned requirement, a primary object of the present invention is to provide a viral vector, whose transcripts induce gene inactivation in plants, which comprises a cDNA sequence reverse transcribed from RNA of Cymbidium mosaic virus (CymMV), and the preferred cDNA sequence is listed as SEQ ID NO: 1.

The preferred viral vector is a recombinant plasmid, more preferably a plasmid comprising pGEMT or its derivatives, such as pGEMT@easy (all are purchased from Promega, USA).

The plants applied with the abovementioned viral vector are not restricted, preferably monocots, more preferably Orchidaceous, and most preferably *Phalaenopsis* spp.

The abovementioned viral vector can further comprise a promoter for expressing a foreign gene, a preferred promoter is a subgenomic promoter for the coat protein of a CymMV, more preferably a subgenomic promoter for the coat protein of a CymMV comprising a sequence of SEQ ID NO: 2. The nucleotide sequence SEQ ID NO: 2 is selected from −100 bp to +21 bp relative to the translation initiation site of the coat protein. Most preferably, a promoter comprises a sequence of SEQ ID NO: 3. The nucleotide sequence SEQ ID NO: 3 is selected from −60 bp to +21 bp relative to the translation initiation site of the coat protein.

Another object of the invention is to provide a method to inactivate plant genes, which comprises the steps of:

(a) obtaining a viral vector comprising a cDNA sequence reverse transcribed from RNA of Cymbidium mosaic virus (CymMV);

(b) constructing a recombinant plasmid containing a homologous gene fragment of the plant and the viral vector;

(c) preparing transcripts of the plasmid through in vitro transcription;

(d) infecting the plant with said transcripts; and (e) forming siRNA from said transcripts to make the homologous gene inactive.

The preferred cDNA sequence in the abovementioned method is listed as SEQ ID NO:1.

The preferred viral vector in the abovementioned method is a recombinant plasmid, more preferably a plasmid comprising pGEMT or its derivatives, such as pGEMT@easy (all are purchased from Promega, USA).

The plants applied in the abovementioned method are not restricted, preferably monocots, more preferably Orchidaceous, and most preferably *Phalaenopsis* spp.

The abovementioned viral vector in the abovementioned method can further comprise a promoter for expressing a foreign gene, a preferred promoter is a subgenomic promoter for the coat protein of a CymMV, more preferably a subgenomic promoter for the coat protein of a CymMV comprising a sequence of SEQ ID NO: 2. The nucleotide sequence SEQ ID NO: 2 is selected from −100 bp to +21 bp relative to the translation initiation site of the coat protein. Most preferably, a promoter comprises a sequence of SEQ ID NO: 3. The nucleotide sequence SEQ ID NO: 3 is selected from −60 bp to +21 bp relative to the translation initiation site of the coat protein.

The homologous gene fragment of the plant in step (b) of the abovementioned method can be a gene related to floral appearance.

The in vitro transcription in step (c) of the abovementioned method can be conducted using RNA polymerase and promoter from phages.

The other object of the invention is to provide a method to change the characteristics of plants, which comprises the steps of:

(a) obtaining a viral vector comprising a cDNA sequence reverse transcribed from RNA of Cymbidium mosaic virus (CymMV);

(b) constructing a recombinant plasmid containing a homologous gene fragment of the plant and the viral vector;

(c) preparing transcripts of the plasmid through in vitro transcription;

(d) infecting the plant with said transcripts; and (e) forming siRNA from said transcripts to inactivate the homologous gene and change the plant characteristics.

The preferred cDNA sequence in the abovementioned method is listed as SEQ ID NO: 1.

The preferred viral vector in the abovementioned method is a recombinant plasmid, more preferably a plasmid comprising pGEMT or its derivatives, such as pGEMT@easy (all are purchased from Promega, USA).

The plants applied in the abovementioned method are not restricted, preferably monocots, more preferably Orchidacea, and most preferably *Phalaenopsis* spp.

The abovementioned viral vector in the abovementioned method can further comprise a promoter for expressing a foreign gene, a preferred promoter is a subgenomic promoter for the coat protein of a CymMV, more preferably a subgenomic promoter for the coat protein of a CymMV comprising a sequence of SEQ ID NO: 2. The nucleotide sequence SEQ ID NO: 2 is selected from the translation initiation site −100 bp to +21 bp of the coat protein. Most preferably, a promoter comprises a sequence and is listed as SEQ ID NO: 3. The nucleotide sequence SEQ ID NO: 3 is selected from the translation initiation site −60 bp to +21 bp of the coat protein.

The homologous gene fragment of the plant in step (b) of the abovementioned method can be a gene related to flower morphology.

The in vitro transcription in step (c) of the abovementioned method can be conducted using RNA polymerase and promoter from phage.

The present invention is further explained in the following embodiment illustration and examples. Those examples below should not, however, be considered to limit the scope of the invention, it is contemplated that modifications will readily occur to those skilled in the art, which modifications will be within the spirit of the invention and the scope of the appended claims.

BRIEF DESCRIPTION OF THE DRAWINGS

The patent or application file contains at least one drawing executed in color. Copies of this patent or patent application publication with color drawing(s) will be provided by the Patent and Trademark Office upon request and payment of the necessary fee.

The related drawings in connection with the detailed description of the present invention to be made later are described briefly as follows, in which:

FIG. 5 shows the detection of CymMV vectors 28 days post inoculation. Northern blot hybridization was conducted using DIG labeled minus sense probe corresponding to CymMV coat protein (A) or 553 nucleotides to the 3'-terminus of GFP gene (B). M: healthy plants; M1: pCymMV-M1; CymMV-pro60-GFP: pCymMV-pro60-GFP; and CymMV-pro100-GFP: pCymMV-pro100-GFP. Transcripts derived from pTMV-GFP30 were used as positive control for GFP hybridization (Virology, 255, 312-23, 1999).

DETAILED DESCRIPTION OF THE PREFERRED EMBODIMENT

Example 1

CymMV Isolation

*Phalaenopsis* spp. orchids were purchased from Taiwan Sugar Company, which have been routinely detected with enzyme linked immunosorbent assay (ELISA) using antibody against CymMV. Healthy looking plants with higher ELISA value were selected and analyzed by RT-PCR using primer pairs of SEQ ID NO: 4 and SEQ ID NO: 5 to confirm the infection of CymMV. Sap from infected plants was used as inoculum and transmitted to *Cassia occidentals*, followed by three consecutive single local lesion isolations to isolate CymMV. *Phalaenopsis* spp. orchids infected with these isolates were maintained in the green house for at least six months. The plants without symptom were analyzed by RT-PCR to confirm the CymMV infection. One isolate from the healthy looking plants was selected for further experiments.

RT-PCR

Unless notified, RNA extracted from CymMV infected plants was used as templates for synthesis of cDNAs using M-MLV reverse transcriptase according to the manufacturer's instruction (RT; Promega Corp., USA). The PCR conditions were as described by Rubio et al. (Proc. Natl. Acad, Sci. U.S.A., 99, 10865-9, 2002). The cDNAs were PCR-amplified in a 20 µl reaction mixture (1.5 mM $MgCl_2$, 1 mM of each of the four dNTPs, 2.5 U of Taq DNA polymerase) containing 50 ng of each oligonucleotide. The PCR cycle were carried out at 94° C. for 4 min, then 30 cycles of 94° C. for 30 seconds; 55° C. for 30 seconds and 72° C. for 1 min, followed by an extension step at 72° C. for 10 min. Symptomless CymMV isolates isolated from *Phalaenopsis* spp. were used to construct the CymMV cDNA-containing vector to prevent the symptoms and physiological changes after CymMV infection.

Construction of CymMV cDNA-Containing Viral Vector

Figure 1:
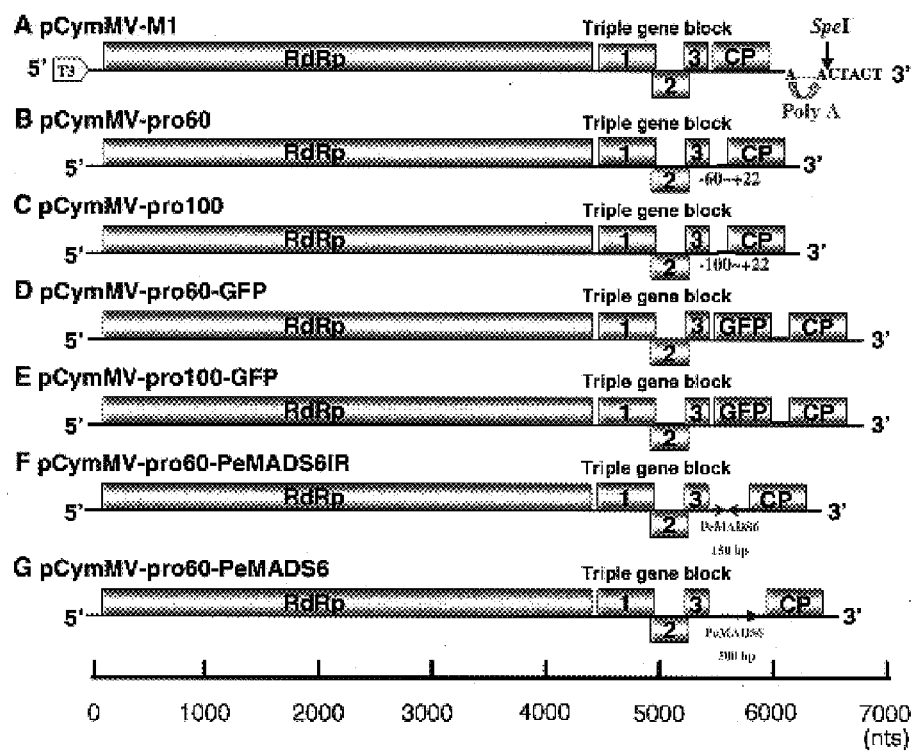
FIG. 1 is schematic representation of viral vectors of the present invention. T3 Promoter is immediately adjacent to the 5'-ends, and a poly A tail (25 adenosines) is close to the 3'-end. SpeI restriction site is indicated with a red arrow. A: pCymMV-M1; B: pCymMV-pro60; C: pCymMV-pro100; D: pCymMV-pro60-GFP; E: pCymMV-pro100-GFP; F: pCymMV-pro60-PeMADS6IR; G: pCymMV-pro60-PeMADS6. Arrow inside the rectangle represents that the conserved PeMADS6 gene is directly subcloned into the plasmid. Rectangles represent ORFs encoded by CymMV genomic RNA. RNA dependent RNA polymerase (RDRP), triple gene block 1, 2, and 3, coat protein (CP) and green fluorescent protein (GFP) are as indicated. Red lines represent the duplicated subgenomic promoters. The plus or minus signs below the red lines are corresponded to upstream and downstream of the CP translation start codon respectively, and numbers indicate the selected region of CP subgenomic promoter. Head to head arrows indicate that the selected 150 bp of PeMADS6 was cloned in the form of inverted repeats. A scale bar in nucleotides is shown at the bottom.

RNA extracted from CymMV infected plants and primer pairs of SEQ ID NO: 6 and SEQ ID NO: 7 were used to synthesize cDNA. Template of the synthesized cDNA and primer pairs of SEQ ID NO: 8 and SEQ ID NO: 6 were used in PCR reaction to amplify the 1-3865 bp of CymMV fragments containing a T3 promoter. Similar reaction was carried out with primer pairs of SEQ ID NO: 9 and SEQ ID NO: 7 to obtain a DNA fragment containing 3783-6226 bp of CymMV with a poly A tail (25 Adenosine) and a SpeI restriction site. Both fragments were cloned into pGEM-T plasmid (Promega Co., USA) by incubating with DNA ligase (Promega Corp., USA) overnight at 4° C., followed by transforming the ligated products into *Eschericia coli*, DH5α competent cells to obtain pCymMV-1 and pCymMV-2 plasmids respectively. Both vectors were digested with NotI and SnaI, analyzed in 1% agarose gels and detected with ethidium bromide staining. The ca. 3.9 kb and 5.4 kb fragments derived from pCymMV-1 and pCymMV-2 digestion respectively were purified by Gel Extraction kit (from Qiagen). The purified fragments were ligated with T4 DNA ligase to construct the cDNA infectious clone, pCymMV-M1 containing the full length of pCymMV cDNA (as shown in FIG. 1A). This plasmid was stored in Food Industry Research and Development Institute (FIRDI) with the number of BCRC 940485 on Sep. 28, 2005.

In Vitro Transcription

Capped transcripts corresponding to wildtype and vectors of CymMV were synthesized with phage RNA polymerase and its promoter according to Yeh et al. (J. Virol., 74, 5762-8, 2000) except that pCymMV-M1 and the derived plasmids were all linearalized by SpeI.

RNA Extraction and Northern Blot Hybridization

RNA used in northern blot analysis and RT-PCR was extracted from plants according to Tian et al. (Mol. Plant Patho., 86, 1167-73, 1996). T7 RNA polymerase and HpaI digested pCymMV-M1 plasmids (corresponding to 590 nucleotides of CymMV 3'-end) were employed to generate negative-sense DIG-labeled probes (Boerhinger Mannheim). Total RNAs were subjected to hybridization according to Klaassen et al. (Virology, 222, 169-75, 1996) using the chemiluminescent substrate, CDP STAR (from Boerhinger Mannheim), and exposing blots to Fuji medical X-ray film to detect positive hybridization reactions.

Figure 2:
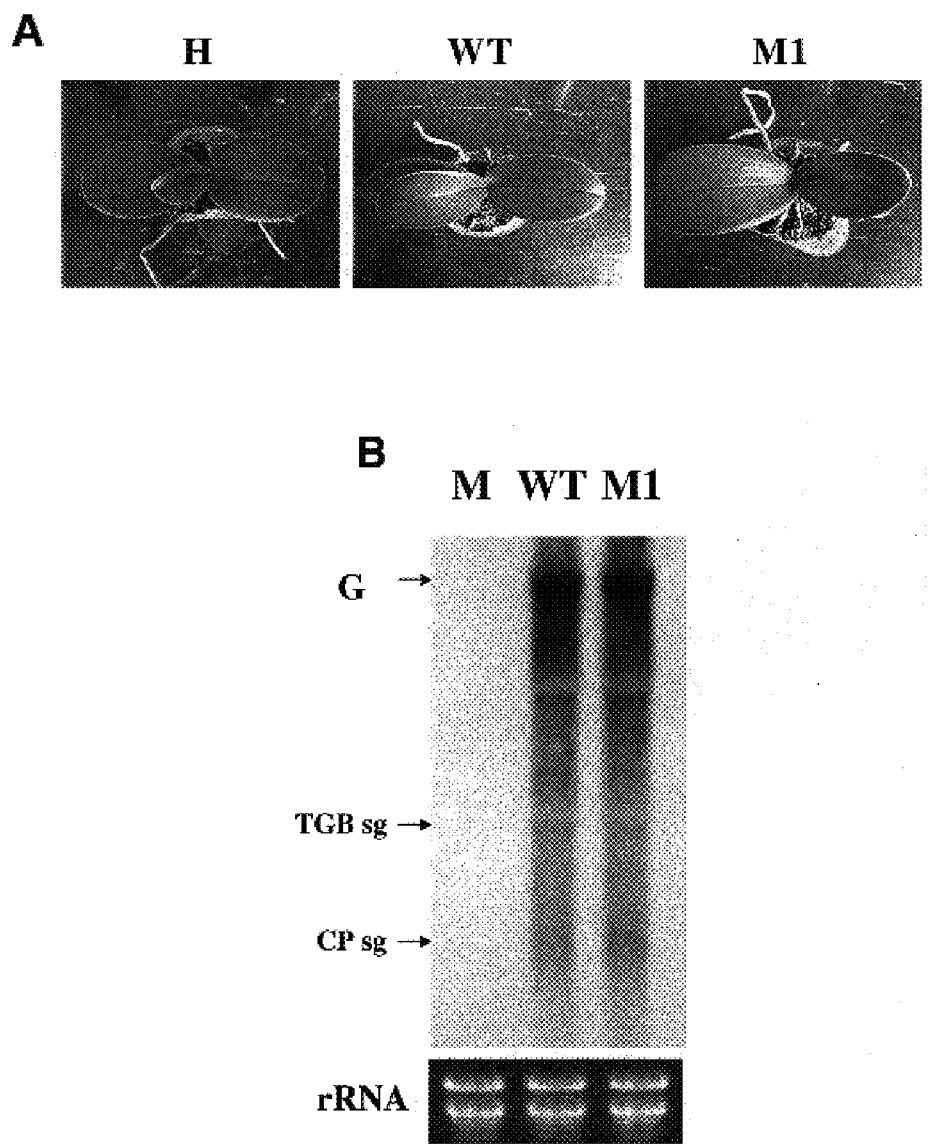
FIG. 2. shows the photos of healthy and CymMV-infected *Phalaenopsis* spp. Photos were taken 6 months post inoculation. B shows the result of Northern blot analysis on CymMV-infected leaves. H: healthy plants; WT: wild type CymMV infected plants; M1: transcripts of CymMV-M 1 infected plants. Total RNA was extracted from CymMV infected leaves and subjected for northern blot hybridization using DIG labeled minus sense probe 590 nucleotides to the 3'-end of CymMV gene. Genomic RNA (G), triple gene block subgenomic RNA (TGB sg) and coat protein subgenomic RNA (CP sg) are as indicated. Ribosomal RNA (rRNA) is loaded as control marker.

FIG. 2A shows that no symptom was observed on both plants inoculated with wild type CymMV or transcripts from the derived vector 6 months post inoculation. Saps extracted from the wild type virus infected plants and transcripts derived from pCymMV-1 were used to inoculate *P. amabilis* to compare the infectivity between them through northern blot analysis 14 days post inoculation. FIG. 2B shows that similar levels of RNA were detected from both plants.

Construction of CymMV Expression Vectors

<Determination of Subgenomic Promoter of CymMV Coat Protein>

Figure 3:
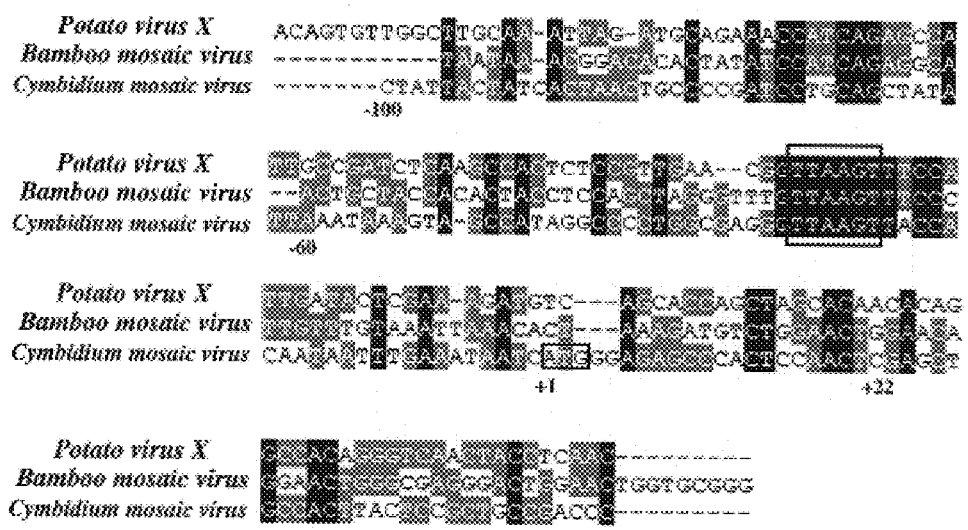
FIG. 3 shows the sequence alignment of predicted subgenomic promoter regions of the coat protein from BaMY (Bamboo mosaic virus) SEQ ID NO: 30, CymMY (Cymbidium mosaic virus) SEQ ID NO: 31 and PYX (Potato virus X) SEQ ID NO: 29. Sequences relative to coat protein translation start site −50 to 100 bp are aligned by Clustal W 1.8. Numbers indicate the CymMY nucleotide position surrounding coat protein translation start site. The CymMY coat protein translation start codon and the highly conserved hexanucleotides are indicated by open rectangles. Based on the alignments, −60 to 21 bp (listed as SEQ ID NO: 3) and −100 to 21 bp (listed as SEQ ID NO: 2) were selected to contain the CymMY coat protein subgenomic promoters, and were used to construct CymMY-derived vectors.

The coat protein subgenomic promoters have been analyzed and compared with those of PVX and Bamboo mosaic virus (BaMV) of the genus Potexvirus. FIG. 3 shows the alignment of coat protein subgenomic promoters (between −50 to 100 bp relative to the coat protein translation start site) of PVX, BaMV and CymMV. Limited similarity was found between −60 to 30 bp. The coat protein subgenomic promoters of PVX and BaMV are located at −60 to 17 bp and −91 to 16 bp respectively (relative to translation start site). Based on the alignments, −60 to 21 bp (listed as SEQ ID NO: 3) and −100 to 21 bp (listed as SEQ ID NO: 2) were selected to contain the CymMV coat protein subgenomic promoters, and were used to construct CymMV-derived vectors.

<Construction of CymMV Expression Vectors>

Template pCymMV-M1 and primer pair of SEQ ID NO: 10 and SEQ ID NO: 7, as well as primer pair of SEQ ID NO: 11 and SEQ ID NO: 9 were used to amplify fragments in PCR reactions respectively. The amplified fragments were gel purified and mixed in a 1:1 ratio to conduct PCR reaction for 5 cycles. Then primer pair of SEQ ID NO: 9 and SEQ ID NO: 7 were added for another 30 cycles. PCR products were digested with NheI and HpaI and loaded into 1% agarose gel to purify a ca. 1.3 kb fragment. In addition, the pCymMV-M1 was also digested with NheI and HpaI and run in 1% agarose gel to purify a ca. 8 kb fragment. These two purified fragments were ligated to construct pCymMV-SmaI plasmid.

Template pCymMV-M1 and primer pair of SEQ ID NO: 12 and SEQ ID NO: 7, as well as primer pair of SEQ ID NO: 13 and SEQ ID NO: 7 were used to amplify fragments in PCR reaction respectively. The PCR products were digested with HpaI, ligated to pCymMV plasmid digested by SmaI and HpaI, and inserted nucleotide sequences of subgenomic promoter for the coat protein listed as SEQ ID NO: 2 and SEQ ID NO: 3 into 5502 bp of SEQ ID NO: 1 to compensate the expression of the coat protein to construct pCymMV-pro100 (FIG. 1C) and pCymM-pro60 (FIG. 1B).

DNA sequence encoding green fluorescence protein (GFP) was introduced into the abovementioned CymMV vector to test the expression ability. Plasmid pBIN-gfp-5-ER containing GFP gene, which was distributed by Dr. Jim Haseloff (gene bank accession number U87974), was served as a template in a PCR reaction containing a primer pair of SEQ ID NO: 14 and SEQ ID NO: 15. The amplified fragments were ligated with SmaI digested pCymMV-pro100 and pCymMV-pro60 respectively to construct pCymMV-pro100-GFP (FIG. 1E) and pCymMV-pro60-GFP (FIG. 1F).

Figure 4:
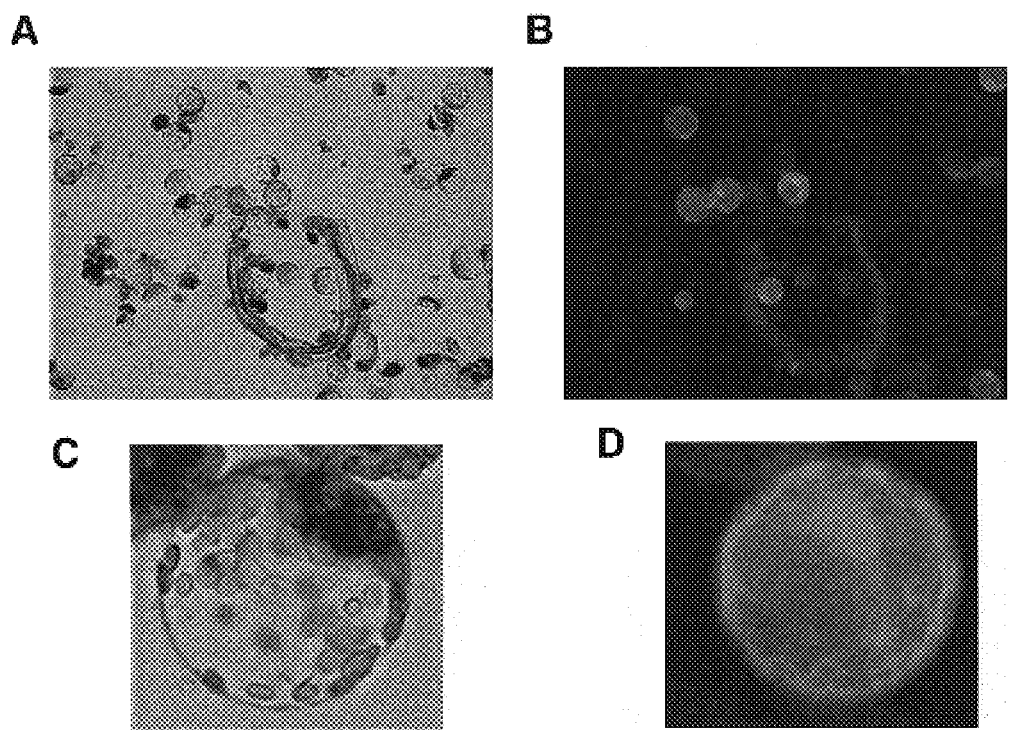
FIG. 4 shows the expression of green fluorescent protein (GFP) in protoplasts inoculated with CymMV vectors containing GFP gene. Transcripts of pCymMV-CP60-GFP were inoculated into $5 \times 10^5$ of *N. benthamina* protoplasts. Cells were examined 48 hrs post inoculation under light (A and C) and fluorescent microscope (B and D).
Figure 6:
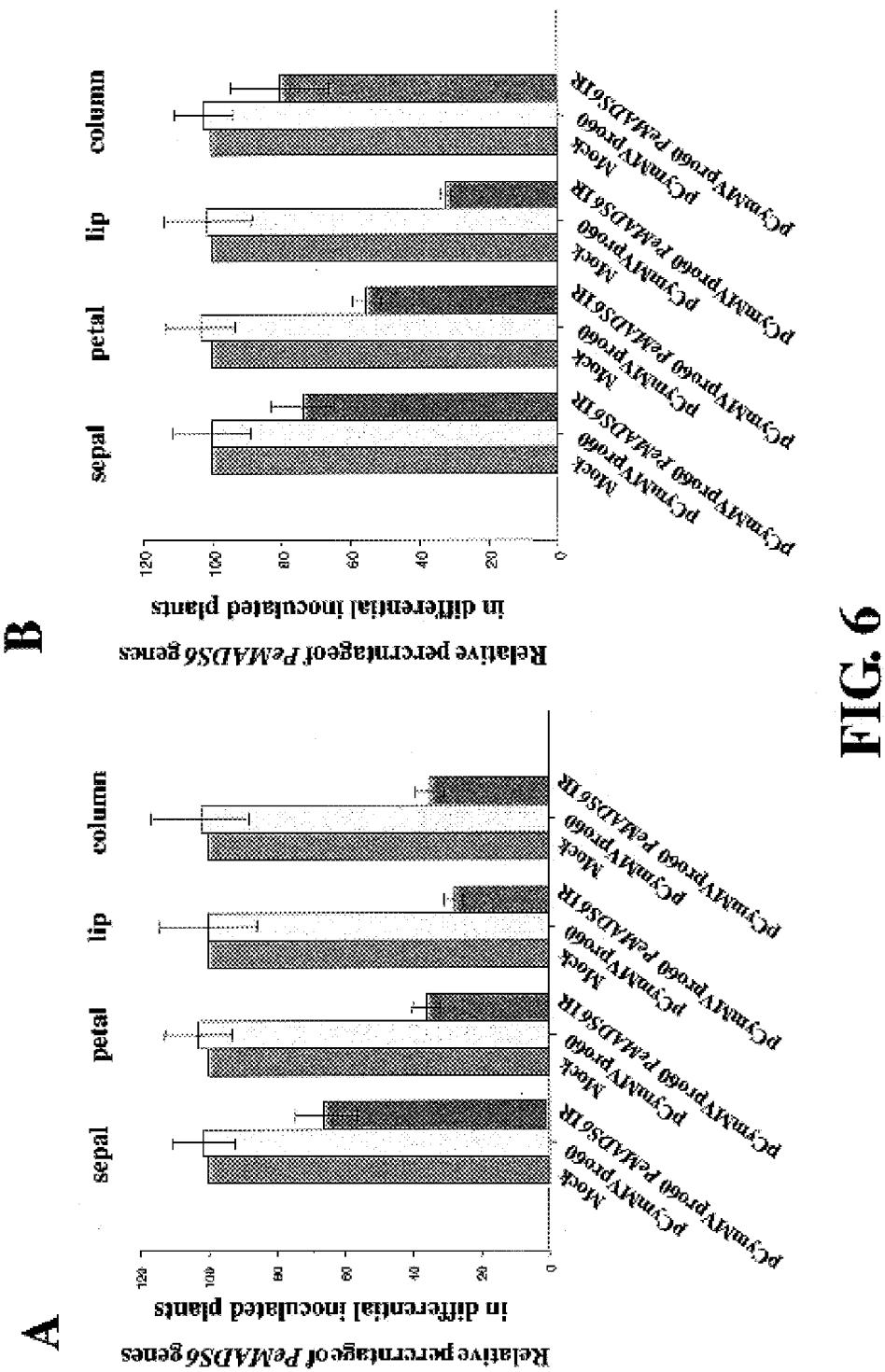
FIG. 6 shows the relative quantification of the MADS-box genes by real-time RT-PCR. Relative quantification of PeMADS6 in *P. amabilis* (A), or *P. Sogo Musadium* (B) infected with buffer (Mock), pCymMV-pro60 or pCymMV-pro60-PeMADS6IR. The PeMADS6 transcript level of plants inoculated with buffer was set at 100% for relative quantification.

Transcripts derived from pCymMV-pro100-GFP and pCymMV-pro60-GFP were inoculated to protoplasts of *N. benthamina* (a natural host for the selected CymMV isolate). As shown in FIG. 4, there was about 20-28% protoplasts emitted bright green fluorescence 14 hrs post inoculation. On the other hand, same amounts of the transcripts derived from pCymMV-M1, pCymMV-pro60-GFP and pCymMV-pro100-GFP were inoculated to leaves of *P. amabilis*. Transcripts derived from both vectors of pCymMV-pro60-GFP and pCymMV-pro100-GFP could systemically infect the whole plant. As shown in FIG. 5, the RNA from GFP gene could be detected through northern blot hybridization 28 days post inoculation.

These results indicated that the selected subgenomic promoter of the coat protein is functional, and the foreign genes in the expression vectors stayed even after 28 days post inoculation. Based on the same viral vector construction, either in the form of plasmid propagated in *E. coli* or as RNA viruses in plants, the longer the duplicated promoter is, the more chance leading to recombination. Therefore, pCymMV-pro60 was a preferred vector for gene silencing induction.

Example 2

Construction of VIGS Vectors

To test if the abovementioned viral vectors could induce gene silencing in plants, a GLOBOSA/PISTILLATA-like gene, PeMADS6 gene, which belongs to the MADS-box gene family, was selected from the established floral EST database of *P. equestris* according to Tsai et al. (Plant Cell Physiol., 45, 831-44, 2004; Plant Cell Physiol., 46, 1125-39, 2005).

To specifically knockdown PeMADS6 gene, a stretch of 150 bp gene fragment located at the 3'-terminus was selected to insert into the pCymMV-pro60 vector. This gene fragment is specific to PeMADS6, which have been used as a probe to detect PeMADS6 without showing cross hybridization (Tsai et al., 2005).

Moreover, Smith et al. (Nature, 407, 319-20, 2000) and Wesley et al. (Plant J., 27, 581-90, 2001) have reported that inverted repeat sequences could enhance the gene silencing. Therefore, the gene fragment was cloned to pCymMV-pro60 in the form of an inverted repeat to generate pCymMV-pro60-PeMADS6IR (FIG. 1F).

PCR reaction containing a primer pair of SEQ ID NO: 16 and SEQ ID NO: 17 and template of SEQ ID NO: 18 was carried out to amplify a 150 nucleotides gene fragment of SEQ ID NO: 19 (corresponding to No. 172-221 codon of PeMADS6 ORF with EcoRI restriction site at both 5'- and 3'-termini). The fragments were gel purified and ligated with SmaI digested pCymMV-pro60 to generate an inverted repeat-containing plasmid pCymMV-pro60-PeMADS6IR.

In addition, 500 nucleotides of the highly conserved MADS box gene family (SEQ ID NO: 20) was subcloned into the pCymMV-pro60 vector to knock down the MADS box gene family. PCR reaction containing primer pair of SEQ ID NO: 21 and SEQ ID NO: 22, and template of pPeMADS6 was carried out to amplify the MADS box gene family conserved region. The fragments were subcloned into pCymMV-pro60 to generate pCymMV-pro60-PeMADS6 (FIG. 1G).

Transcripts derived from pCymMV-pro60, pCymMV-pro60-PeMADS6-IR, and pCymMV-pro60-PeMADS6 vectors were inoculated on to emerging stalks of *P. amabilis* respectively. The knockdown effects were compared after 45 days.

Real-Time Quantitative RT-PCR

Different parts of flowers such as sepal, petal, lip and coloum from healthy plants and plants inoculated with transcripts of pCymMV-pro60, pCymMV-pro60-PeMADS6IR or pCymMV-pro60-PeMADS6-inoculated plants were dissected and subjected to RNA quantification of PeMADS6IR gene through real-time PCR analysis. Total RNA was extracted as described by Chang (Plant Mol. Biol. Rep., 155, 113-6, 1993) and dissolved in 50 μl of DEPC treated $H_2O$. The RNA was digested with RNAse free DNAase (from Ambion) at 37° C. for 2 hour, followed by phenol:chloroform:isoamyl alcohol (25:24:1) extraction to remove genomic DNA. Five μl of RNA was served as a template for synthesis of cDNAs using M-MLV reverse transcriptase according to the manufacturer's instruction (Promega Co., USA). One fourth of the cDNA was mixed with 2 volumes of SYBR Green PCR Master Mix (PE Applied Biosystems) for quantitative PCR analysis using an ABI Prism 7000 Sequence Detection System according to the manufacturer's instruction (PE Applied Biosystems). The primer pair of SEQ ID NO: 23 and SEQ ID NO: 24 was used for PeMADS6 amplification of pCymMV-pro60-PeMADS6IR inoculated plants. The primer pair of SEQ ID NO: 27 and SEQ ID NO: 28 was used for PeMADS6 amplification of pCymMV-pro60-PeMADS6 inoculated plants. Each sample was quantitatively standardized through amplification of Ubiqutin cDNA using the primer pair of SEQ ID NO: 25 and SEQ ID NO: 26. Dissociation curves were generated to confirm the amplification of single product (both PeMADS6 and Ubiqutin). Additional Real-time PCR reactions, with no template cDNA, or RNA only (without reverse transcription) were conducted as control groups to confirm that there was no contaminating genomic DNA. For each real-time RT-PCR analysis, triplicate samples of RNA were analyzed.

Figure 7:
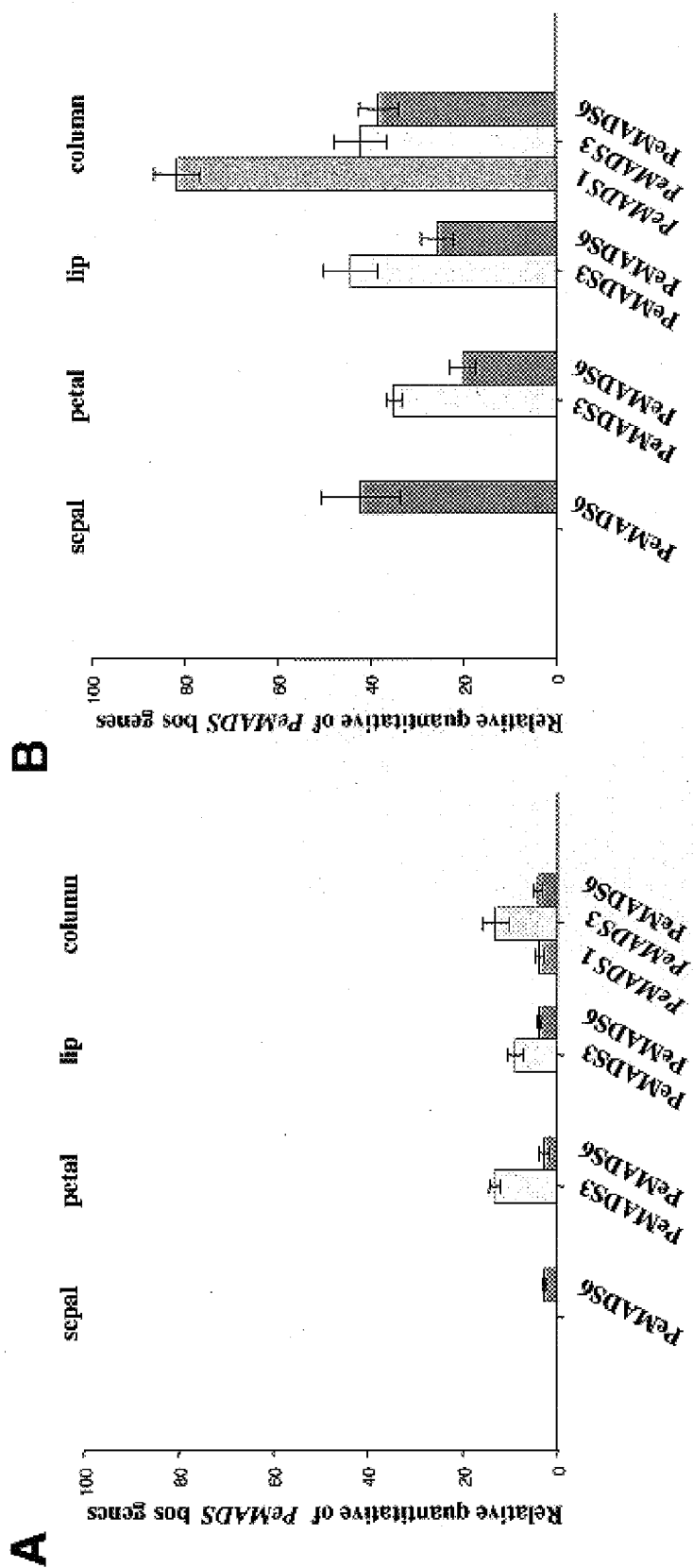
FIG. 7 shows the relative quantification of the MADS-box genes by real-time RT-PCR. Relative quantification of PeMADS1, PeMADS3 and PeMADS6 transcripts in flower buds (C) or flowers (D) of *P. Sogo Musadium* infected with pCymMV-pro60-PeMADS6. The PeMADS1, PeMADS3 and PeMADS6 transcript levels in flower buds or flowers of plants inoculated with buffer were set at 100% for relative quantification of each gene.

FIG. 7 shows similar amounts of PeMADS6 RNA levels of each flower parts from both mock and wildtype virus (transcripts of pCymMV-pro60) inoculated plants. In contrast, the PeMADS6 RNA levels in the PeMADS6 RNA levels in sepals, petals, lips and columns of plants inoculated with pCymMV-pro60-PeMADS6IR were all reduced (FIGS. 7A and 7B). The PeMADS6 RNA level was reduced to 63±2%, 33±3%, 23±5% and 33±2 in sepals, petals, lips and columns, respectively, in *P. amabilis* (FIG. 7A), and 73.5±6.5%, 55±3%, 32±1% and 80±10% in *P. Sogo Musadium* (FIG. 7B). We also analyzed the RNA level of PeMADS1 and PeMADS3 belonging to C- and B-class-like MADS-box genes in plants inoculated with pCymMV-pro60-PeMADS6IR. In contrast, no obvious transcriptional changes in PeMADS1 and PeMADS3 were detected between the plants inoculated with buffer or pCymMV-pro60 or pCymMV-pro60-PeMADS6IR. Thus, the knock down of PeMADS6 in plants inoculated with pCymMV-pro60-PeMADS6IR was specific.

Figure 8:
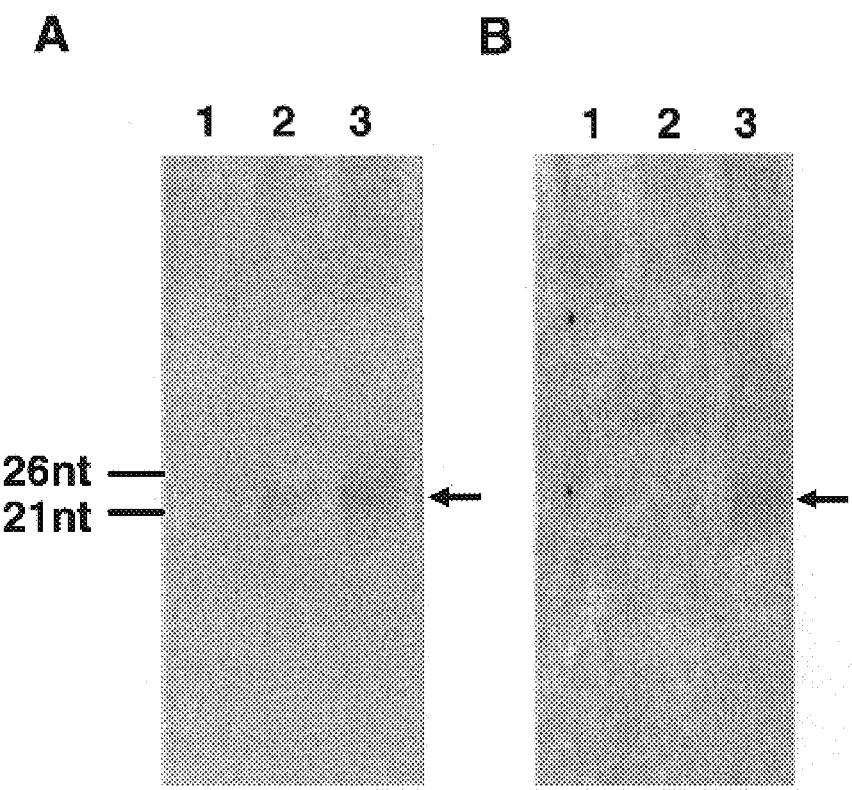
FIG. 8 shows the detection of siRNA. siRNA were detected with Northern blot hybridization using a DIG labeled minus sense RNA probe corresponding 533 nucleotides to the 3'-terminus of CymMV gene (A) or DNA probes corresponding to PeMADS6 (B). Small molecular weight nucleic acids purified from healthy plants (lane 1), plants inoculated with transcripts derived from pCymMV-pro60 (lane 2) or plants inoculated with transcripts derived from pCymMV-pro60-PeMADS6IR (lane 3).

FIG. 8 reveals that the transcription levels of PeMADS1, PeMADS3 and PeMADS6 were all silenced in plants inoculated with transcripts derived from pCymMV-pro60-PeMADS6 (FIGS. 8A and 8B). The reduced levels were more prominent in flower buds than in flowers. For PeMADS1, PeMADS3 and PeMADS6, more than 90% of the transcription level was reduced in flower buds.

Detection of siRNA

To prove that the amount of PeMADS6 RNA decrease is caused by RNA interference (RNAi), small molecular weight RNA from healthy *Phalaenopsis* spp. without inoculation, transcripts of pCymMV-pro60 vector inoculated *Phalaenopsis* spp. and transcripts of pCymMV-pro60-PeMADS6IR vector inoculated *Phalaenopsis* spp. was isolated respectively and analyzed with Northern blot using probes of the gene of a CymMV coat protein or PeMADS6 gene.

The detection of siRNA was according to Hamilton and Baulcombe (Science, 286, 950-2, 1999) with some modifications. Total RNA was extracted from flowers of *P. amabilis* as described by Chang (Plant Mol. Biol. Rep., 155, 113-6, 1993) except that 1/10 (V/V) volume of 3M Sodium acetate pH 5.2 was used to precipitate total nucleic acids. Low molecular weight RNA was enriched by precipitation with 5% polyethylene glycol 8000-0.5 M NaCl. The RNA was separated, transferred and fixed onto filter. Prehybridization was conducted at 35° C. for 2 hour as described (Hamilton and Baulcombe, 1999). Hybridization was carried out in the same solution containing DIG-labeled probes of minus sense CymMV 3' terminus RNA or DIG-labeled random primer probes using PCR amplified PeMADS6 (amplified by primer pair SEQ ID NO: 19 and SEQ ID NO: 17, and template pPeMADS6 for 16 hours at 35° C. The membrane was washed twice by 2× SSC and 0.2% SDS at room temperature. In vitro transcription was performed using T7 Polymerase and AvaI and BamHI digested pGEMT3ZF (+) (Promega Corp., USA) as templates to generate 21 and 26 nucleotide-RNA oligonucleotides respectively. These RNAs were separated on the same gel as marker, stained with ethidium bromide and imaged.

Figure 9:
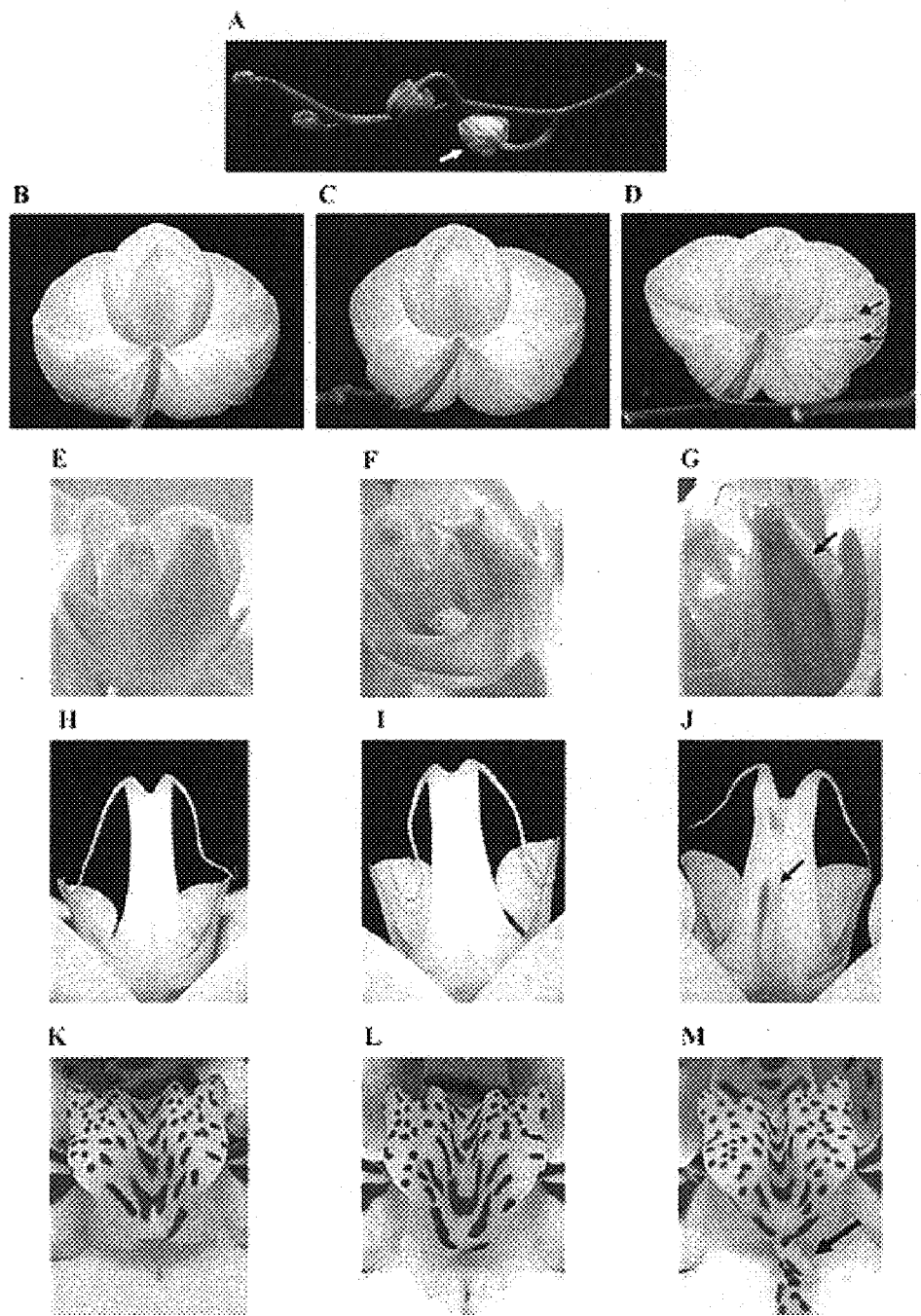
FIG. 9 shows plants infected with buffer (B, E, H and K), pCymMV-pro60 (C, F, I and L) and pCymMV-CP60-Pe-MADS6 (A, D, G, J and M). E, F and G, *P. amabilis*; the rest *P. Sogo Musadium*. The arrow on A indicates the aborted flower buds, flower buds produced below this node were all aborted, and flower buds produced beyond this node blossomed. The arrows on G indicate the greenish streaks of the flower. The arrows on G and J indicate the greenish patches of the lip. The arrow on M indicates the elongated appendix.

Lane 1 of FIGS. 9, A and B shows that no siRNA was detected in healthy plants without inoculation. The siRNA ca. 21-nucleotide in length was detected in plants inoculated with transcripts derived from pCymMV-pro60 and pCymMV-pro60-PeMADS6IR using CymMV coat protein gene as probe (FIG. 9, A, lane 2 and 3), while the siRNA analyzed with Northern blot using the PeMADS6 gene as probe was only detected in plants inoculated with transcripts derived from pCymMV-pro60-PeMADS-IR (FIG. 9, B, lane 3) but not from plants inoculated with transcripts derived from pCymMV-pro60 (FIG. 9, B, lane 2). In summary, the CymMV VIGS vector generated siRNA only when the homologous gene fragment of PeMADS6 was inserted into the CymMV derived vectors. Therefore, the reduced PeMADS6 level is indeed caused by gene inactivation through gene silencing mechanism.

Morphological Changes Induced by Viral Vectors

Although the CymMV vector induced PeMADS6 gene silencing in every floral organ of plants inoculated with pCymMV-pro60-PeMADS6IR, yet no obvious morphology changes were observed. It is likely that the knockdown level induced by VIGS might not have been enough to induce flower morphology change and more possibly that other genes may compensate for the knockdown effect of PeMADS6. However, the CymMV vector was able to knockdown MADS-box family gene simultaneously and cause prominent morphology.

*P. amabilis* and *P. Sogo Musadium* inoculated with pCymMV-pro60-PeMADS6 Produced flower buds on the lower stalks initially; however, these buds were unable to blossom (FIG. 10A and data not shown). Interestingly, in some plants inoculated with pCymMV-pro60-PeMADS6, the flower buds produced on the upper stalk blossomed, but streaks or patches of greenish tissues were observed in sepals, petals and lips (FIG. 10, B-J). The greenish streaks or patches were more prominent in the adaxial than the adaxial side. All these phenotypes were observed on both varieties, except greenish streaks were found more frequently in sepals and petals of *P. Sogo Musadium* (FIG. 10, B-J). Surprisingly, an appendix extending from the lip callus was observed only on all blossomed flowers of *P. Sogo Musadium* inoculated with pCymMV-pro60-PeMADS6 (FIG. 10M) and not observed on mock-inoculated plants or plants inoculated with pCymMV-pro60 (FIGS. 10K and 10L).

Though the explanation and the above embodiments, the viral vectors constructed in the present invention could shorten the time needed for function analysis of floral genes in *Phalaenopsis* spp. from at least 2 years to approximately 45 days. Therefore, it could be applied in large-scale gene function analysis in plants. In addition, the viral vector in the invention can inhibit target gene expression after seed germination. It also could be applied easily to study plants with large genome size, long life cycle and even multiploid genome. The viral vectors are of great commercial values, especially towards flower morphology traits with high commercial values.

What is claimed is:

1. A viral vector whose transcripts induce gene inactivation in an orchid, comprising a cDNA sequence of RNA from Cymbidium mosaic virus (CymMV) and a promoter for expressing a foreign gene; wherein said cDNA sequence is SEQ ID NO:1, and said promoter is a subgenomic promoter for coat protein of CymMV.

2. The viral vector as claimed in claim 1, wherein said orchid is a *Phalaenopsis* spp.

3. The viral vector as claimed in claim 1, wherein said promoter is SEQ ID NO: 3.

4. The viral vector as claimed in claim 1, further comprises a homologous gene fragment of said orchid.

5. The viral vector as claimed in claim 4, wherein said orchid is a *Phalaenopsis* spp.

* * * * *